US005645830A

United States Patent [19]
Reid et al.

[11] Patent Number: 5,645,830
[45] Date of Patent: Jul. 8, 1997

[54] LACTOBACILLUS AND SKIM MILK COMPOSITIONS AND METHODS FOR PREVENTING MICROBIAL UROGENITAL INFECTIONS

[75] Inventors: Gregor Reid, London; Andrew W. Bruce, Toronto, both of Canada

[73] Assignee: Research Corporation Technologies, Inc., Tucson, Ariz.

[21] Appl. No.: 244,096

[22] PCT Filed: Nov. 13, 1992

[86] PCT No.: PCT/CA92/00491

§ 371 Date: Sep. 19, 1994

§ 102(e) Date: Sep. 19, 1994

[87] PCT Pub. No.: WO93/09793

PCT Pub. Date: May 27, 1993

[30] Foreign Application Priority Data

Nov. 15, 1991 [GB] United Kingdom ............... 9124335

[51] Int. Cl.$^6$ .................. A61K 35/20; C12N 1/20
[52] U.S. Cl. ............... 424/93.45; 424/430; 424/535; 514/968; 435/252.9; 435/853; 435/854; 435/855; 435/856; 435/857
[58] Field of Search ............... 435/252.9, 853, 435/854, 855, 856, 857; 424/93.45, 433, 430, 535; 426/558; 514/968

[56] References Cited

U.S. PATENT DOCUMENTS

| | | | |
|---|---|---|---|
| 4,259,314 | 3/1981 | Lowey | 424/19 |
| 4,579,734 | 4/1986 | Hata et al. | 424/93 |
| 4,606,919 | 8/1986 | Stojkovic et al. | 424/92 |
| 5,145,853 | 9/1992 | Metzger et al. | 514/254 |
| 5,149,532 | 9/1992 | Brunell | 424/89 |
| 5,176,911 | 1/1993 | Tosi et al. | 424/93 J |
| 5,198,419 | 3/1993 | Ando et al. | 514/8 |
| 5,308,618 | 5/1994 | Konno et al. | 424/195.1 |
| 5,464,755 | 11/1995 | Bochner | 435/34 |

FOREIGN PATENT DOCUMENTS

| | | |
|---|---|---|
| 2622452 | 5/1989 | France . |
| 2041242 | 7/1971 | Germany . |
| 60123 | 5/1983 | Israel . |
| WO/84/04675 | 12/1984 | WIPO . |

OTHER PUBLICATIONS

Hanson, L.A., Archives of Disease in Childhood, vol. 51, pp. 737–743 1976.

Cheong, I.T., Military Medicine, vol. 147, pp. 202–204 Mar. 1982.

Fennell, R.S. et al., Pediatric Research, vol. 10(4), p. 346, abstract #273 Apr. 1976.

English translation of French publication #2,622,452.

Leigh, D.A. et al., "Journal of Antimicrobial Chemotherapy," vol. 23(2), pp. 267–273 Feb. 1989.

Coppa, G.V. et al, "The Lancet," vol. 335, pp. 569–571 1990.

Hawthorn, L.A. et al, "Journal of Biomedical Materials Research," vol. 24, pp. 39–46 1990.

Bruce, A.W. et al, "Can. J. Microbiol.," vol. 43(3), pp. 339–343 Mar. 1988.

International Urogynecology Journal vol. 3, No. 1, 1992 pp. 22–25 Bruce, A. W. et al.

*Primary Examiner*—Michael G. Wityshyn
*Assistant Examiner*—Kristin Larson
*Attorney, Agent, or Firm*—Scully, Scott, Murphy & Presser

[57] ABSTRACT

This invention relates to Lactobacillus, skim milk, Lactobacillus Growth Factor (LGF) and Lactobacillus compositions and methods of employing the compositions for preventing urogenital infections. More particularly, this invention relates to the ability of strains of hydrophobic or hydrophilic Lactobacillus to adhere to biomaterials, and intestinal, vaginal and uroepithelial cells, to resist the action of certain antimicrobial agents and to dominate the urogenital flora.

16 Claims, 1 Drawing Sheet

LACTOBACILLUS AND SKIM MILK COMPOSITIONS AND METHODS FOR PREVENTING MICROBIAL UROGENITAL INFECTIONS

FIELD OF THE INVENTION

This invention relates to compositions and methods employing said compositions for preventing urogenital tract infections.

BACKGROUND TO THE INVENTION

It is well known that indigenous, non-pathogenic bacteria predominate on intestinal, vaginal and uro-epithelial cells and associated mucus in the healthy state, and that pathogenic organisms (such as bacteria, yeast, viruses) predominate in the stages leading to and during infections. Organisms such as Escherichia coli, enterococci, candida, Gardnerella and Klebsiella originate from the bowel, colonize the perineum, vagina, urethra and can infect the bladder and vagina. Treatment with antimicrobial agents is required to eradicate the organisms. However, infections can and do recur, for the urinary tract in an estimated 80% of cases. Prolonged use of antimicrobial agents creates drug resistant pathogens, breakthrough infections and a disruption of the normal flora. The possibility that indigenous bacteria have a role in preventing infection has been postulated for many years, but few studies have been carried out to identify specific bacteria and their properties required for such an effect. U.S. Pat. No. 4,314,995 to Hata et al. investigated anaerobic, lactobacilli-like organisms as a means of treating a number of infectious diseases, but no consideration was given to the combined importance of their hydrophobicity, hydrophillicity, adhesiveness to biomaterials, epithelial cells, mucus and tissues, and no discussion was included to prevent urogenital infections. U.S. Pat. No. 4,347,240 to Mutai et al. discloses a composition and method employing a specific strain of lactobacilli to inhibit tumour growth.

In recent years, our group has investigated the use of lactobacillus to prevent recurrent urinary tract infections, particularly in adult women. Our conclusion has been that the ability of lactobacilli to adhere, inhibit, competitively exclude and coaggregate formed the basis for the protection of the host. However, new and more important information has now come to light, further to human and experimental studies. The invention now takes into account a new infectious state (post-antimicrobial urogenital infections) as distinct from simple urinary tract infection. The former is initiated following use of antimicrobial agents. This application was not obvious previously, as previous literature has concentrated on virulence characteristics of pathogens causing problems, ignoring the fact that recurrences can follow the use of external agents. We previously recognized resistance to NONOXYNOL-9® as being important for selection of lactobacillus. However, the usage of this agent is not universal, and just because a strain can resist its action does not infer that it offers every lactobacillus strain the crucial component of protecting the host.

The ability of lactobacillus to produce inhibitory substances has been believed by us to be important. One obvious such product would be hydrogen peroxide. However, based upon our latest findings, this property is present in strains that do and those that do not protect women from reinfection. Thus, inhibitory activity is not the primary mechanism for prevention of infection.

The adherence of lactobacillus to epithelial cells has been regarded as important in the context of blocking access of pathogens to surfaces. However, what was not recognized previously was the hydrophobic and hydrophillic properties of these strains and the production of proteinaceous adhesions into the environment (supernatant). These new findings were not obvious and in fact describe totally new methods whereby lactobacilli colonize biomaterial and human cell surfaces. The use of intestinal cell monolayers has provided a system more closely related to the in vivo situation, showing that colonization of the intestine (to compete with uropathogenic organisms before they emerge to colonize the urogenital tract and infect the bladder and vagina) must reach higher levels (10 to 165 lactobacillus per cell) to achieve potential protection.

In addition, we now realise that the in vitro adherence levels for lactobacillus to uroepithelial cells bear little resemblance to those found in the in vivo situation, when compared directly. In other words, a count of 65 bacteria per cell in vitro does not always give a count of 65 per cell in vivo. All it can show is that the strain has adhesion potential. In fact, we now know that a level of >0 bacteria per vaginal cell in vivo (along with evidence of some adhesion on cells even when the mean is zero), and a viable count of >100 lactobacillus per ml from a tissue swab, is a preferred characteristic to measure adhesion. The preferred characteristic for the desired result is for a strain to colonize the surface and retain viability and reproduce.

A better understanding of the species of lactobacilli in the vagina has now been acquired by us. In addition, new strains have been examined for various parameters, and their origin, type, identity and properties were not previously known or assumed.

We previously recognized that lactobacillus adhesion to urinary catheters could provide a mechanism for protecting a catheterized patient against urinary tract infection. Infections in these patients are widespread and can be fatal, especially in an acute care setting. Data has been accumulated (Hawthorn and Reid, "Exclusion of uropathogen adhesion to polymer surfaces by Lactobacillus acidophilus", Journal of Biomedical Materials Research, Vol. 24, 39–46 (1990)) to further support the theory that lactobacillus coated onto a catheter can prevent uropathogenic bacteria from adhering. However, the practicality of adhering lactobacillus to a prosthetic device in a manner that would provide a stable product was not obvious, nor was it investigated. Rather, the new information on lactobacillus demonstrates that catheter colonization should come via hydrophobic and hydrophillic adhesion of the organisms to the urethra, from where they themselves will attach to the catheter. This new approach is a significant deviation from the published works, as it takes account of the new lactobacillus properties and the knowledge that catheters are either hydrophobic (TFX silicone) or hydrophillic (Bard and Kendal Foley Lubricated catheters). It also provides a new concept, whereby the lactobacilli do not block uropathogenic adherence as the main means of protecting the host directly, but rather they bind with the uropathogens and form a more normal flora that is less able to infect the host.

The use of skim milk as a potential carrier for lactobacillus was previously considered by us. However, no investigations had been carried out with this substance. In addition, the material was seen as a neutral component that, if anything, would provide a lactobacillus preparation with stability and growth potential in the host. What was not appreciated and what has now been discovered is that specially prepared skim milk and other specific lactobacillus growth factors, called LGF, can be used to stimulate the growth of a patient's own normal flora, to the extent that it could protect the patient against urogenital infection.

By "specially prepared skim milk" is meant skim milk suspended in phosphate buffered saline, autoclaved to eradicate proteinaceous and living contaminants, then freeze dried. By "specific lactobacillus growth factors" is meant substances which stimulate preferentially only growth of lactobacillus and not uropathogens, or alternatively which stimulate significantly more lactobacillus than uropathogen growth. These latter substances are present in skim milk power, lactobacillus microbiological growth media and in other composite compounds and elsewhere.

SUMMARY OF THE INVENTION

The present invention provides a method for the prevention of post-antimicrobial infections caused by pathogenic organisms which comprises administering skim milk powder vaginal suppositories, LGF or an amount of hydrophobic and/or hydrophillic lactobacillus which have a contact angle with water >19 degrees, which are highly adherent to biomaterials, and intestinal, vaginal and uro-epithelial cells, which are resistant to certain antimicrobial agents and which dominate the urogenital flora.

The invention utilizes safe and effective amounts of one or more of the said aforementioned skim milk LGF substance or lactobacilli in a pharmaceutically acceptable carrier. The actual composition can be instilled in the form of a freeze dried preparation, cream, paste, gel, liquid or suppository for intestinal, oral, vaginal, urethral or periurethral instillation.

By "safe and effective" as used herein is meant an amount high enough to significantly positively modify the condition to be treated but low enough to avoid serious side effects (at a reasonable benefit/risk ratio) within the scope of sound medical judgement. The safe and effective amount will vary with the particular condition being treated, the severity of the condition, the age and physical condition of the patient, and the type of preparation or lactobacillus being used.

In the practice of the method as hereinabove defined the lactobacillus may be administered as viable whole cells. The lactobacillus species may be aerobically grown, preferably selected from the group consisting of L. casei, L. acidophilus, L. plantarum, L. fermentum, L. jensenii, L. gasseri, L. cellobiosus, L. crispatus, and L. brevis, more particularly, selected from the group consisting of L. casei var rhamnosus GR-1 (ATCC 55826), L. fermentum B-54 (ATCC 55884), L. casei RC-17 (ATCC 55825), RC-15, 55, 8, 70, 36 (ATCC 55841), 62, 65, L. acidophilus RC-14 (ATCC 55845), 68, 75, L. plantarum RC-20 (ATCC 55883), RC-6, L. jensenii RC-28 (ATCC 55918), L. casei RC-15, and L. gasseri 60 (ATCC 55844).

The lactobacillus species may be microaerophillically grown, preferably, selected from the group consisting of L. casei, L. acidophilus, L. plantarum, L. fermentum, L. jensenii, L. gasseri, L. cellobliosus, L. crispatus, and L. brevis, more particularly, selected from the group consisting of L. casei var rhamnosus GR-1 (ATCC 55826), L. fermentum B-54 (ATCC 55844), L. casei RC-17 (ATCC 55825), RC-15, 55, 8, 70, 36 (ATCC 55841), 62, 65, L. acidophilus RC-14 (ATCC 55845), 68, 75, L. plantarum RC-20 (ATCC 55883), RC-6, L. jensenii RC-28 (ATCC 55918), L. casei RC-15, and L. gasseri 60 (ATCC 55844).

The infection may be associated with the use of a urinary catheter or other prosthetic device.

In further aspects, the invention provides a method for the prevention of urinary tract infections of a mammal in need of such treatment which comprises coating at least a portion of the urogenital tract and/or biomaterial prosthesis with lactobacillus, skim milk or LGF; and a method for the prevention of urinary tract infections of a mammal which utilizes a composition comprising lactobacillus organisms, skim milk or LGF within a suitable pharmaceutically acceptable carrier.

The pharmaceutically acceptable carrier may be in the form of a gelatin suppository, especially useful for oral and/or vaginal implantation, and comprise skim milk or LGF in powder or other form.

The lactobacillus of use in the practice of the invention further preferably attaches to human epithelial cells to a level of 10 to 165 organisms per cell; and wherein the mechanism of adhesion of lactobacillus involves hydrophobic or hydrophillic interactions and involves non-proteinaceous cell wall adhesions on the lactobacillus and proteinaceous adhesions in the surrounding supernatants.

In a more preferred aspect, the invention provides a method to prevent post-antimicrobial urogenital infections caused by pathogenic organisms which method comprises administering an amount of skim milk, LGF, lactobacillus, or supernatant within a pharmaceutically acceptable carrier.

Preferably, the pathogenic organisms are bacteria or fungi.

In a most preferred aspect, the invention provides a method to prevent recurrent urogenital infections in mammals caused by pathogenic organisms which method comprises the steps of (a) administering an effective amount of a urogenital antimiobial agent to substantially eradicate said pathogenic organisms; and (b) administering an effective amount of skim milk powder vaginal suppository, LGF or hydrophobic and/or hydrophillic lactobacillus which have a contact angle with water $\geq 19$ degrees, which colonize biomaterials, intestinal, vaginal and uroepithelial cells, which are resistant to said antimicrobial agent, and which dominate the urogenital flora.

In a further aspect of the invention the method comprises administering said urogenital antimicrobial agent in admixture with said skim milk and/or LGF and/or lactobacillus.

An example of such an admixture is a suppository containing 0.25 g freeze dried lactobacillus, plus 0.25 g specially prepared skim milk powder or LGF plus 160 mg trimethoprim plus 800 mg sulfamethoxazole. Alternatively, it contains 0.25 g freeze dried lactobacillus, plus 0.25 g specially prepared skim milk powder or LGF, plus 400 mg norfloxacin. Other antimicrobial agents include those used to treat urinary tract infections, namely: penicillins, beta-lactams, aminoglycosides, cephalosporins, tetracyclines, nitrofurantoins, fluoroquinolones, as well as other agents and combinations, in addition to nystatin, estrogen and NONOXYNOL-9®. These suppositories are administered preferably by oral route but also by vaginal route, in an appropriate amount and for a suitable duration to have the desired effect (for example, twice daily for three to seven days).

Accordingly, the invention further provides a pharmaceutical composition comprising said urogenital antimicrobial agent in admixture with said skim milk and/or lactobacillus and/or LGF and, optionally, a pharmaceutically acceptable carrier, therefor.

Thus, the invention provides novel methods of preventing post-antimicrobial urogenital infection by either the two-step method defined, hereinabove, or by the above single step incorporating the concurrent eradication of antimicrobial susceptible pathogenic organisms by said antimicrobial agent together with enhancement of the natural flora over said pathogenic organism resistant to said antimicrobial agent by the presence of said skim milk, LGF or lactobacillus.

Examples of urogenital antimicrobial agents of use in the practice of the invention are nonfloxacin and trimethoprim/sulfamethoxazole (TMP/SMX or co-trimoxazole).

Each of the ingredients, antimicrobial agent, skim milk, LGF and lactobacillus strains are provided during the method in sufficient amounts to effect treatment. Such amounts and methods of applications required reside within the skill of the art.

DETAILED DESCRIPTION OF THE INVENTION

The invention will now be illustrated by means of the following non-limiting examples:

EXAMPLE 1

Figure 1:
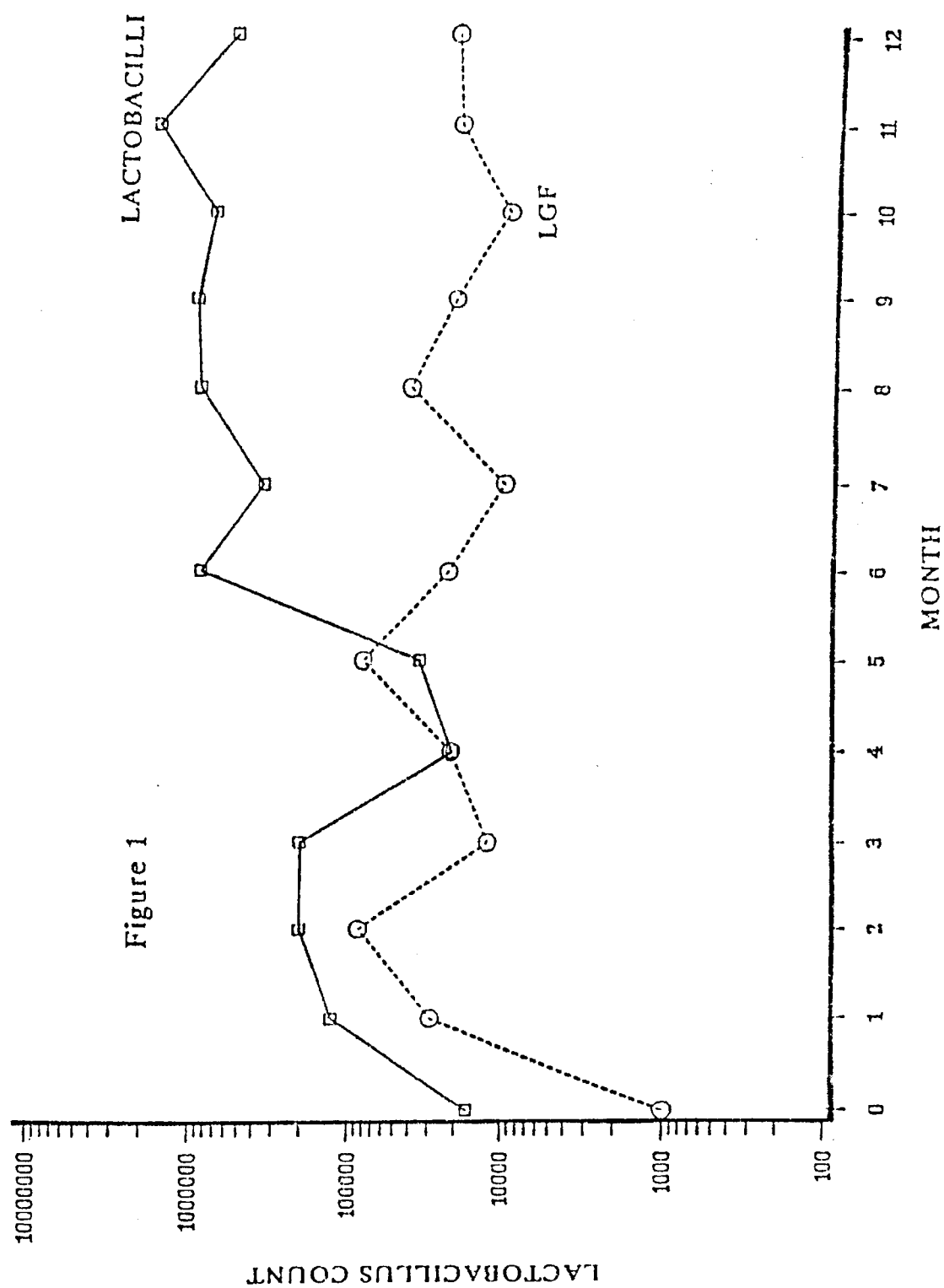
FIG. 1 illustrates the number of lactobacillus per ml isolated from vaginal swabs taken from the two patient groups during the 12 month study of Example 2.

In order to verify that lactobacillus suppositories and skim milk suppositories can reduce the recurrence of urinary tract and vaginal infections, a study was performed on 40 patients. Each patient had urinary tract infection and was treated with 3 days antimicrobial therapy (norfloxacin or co-trimoxazole) then given one vaginal suppository immediately after cessation of therapy. The gelatin suppository contained >$10^9$ viable L. casei GR-1 (ATCC 55826) and L. fermentum B-54 (ATCC 55884) which are known to adhere to cells and produce inhibitory products against uropathogenic organisms. Control patients received specially prepared skim milk powder in the same capsules at the same dosage. The suppositories were given two times a week for two weeks, then only once at the end of the first and second month. The recurrence rate after six months was expected to be over 60% based upon literature reports. The results showed:

Recurrence rate with lactobacillus suppositories=21%

Recurrence rate with specially prepared skim milk suppositories=47%

More recurrences occurred after co-trimoxazole therapy 41% than after norfloxacin therapy 29%.

In more detail, the materials and methods were as follows:

Patients

Forty-one premenopausal women, mean age 23 (±4.4) years, entered the study via one of two university outpatient clinics. Patients were not included in the study if they were pregnant or diabetic; if they had known allergies to fluoroquinolones or TMP/SMX or a history of urinary cancer or other complications associated with the urinary tract (eg. urinary obstruction); or if they were taking any medications other than those used in the study. Patients were included in the study if they showed signs and symptoms of acute lower UTI with dysuria, frequency, urgency, or nocturia, but no flank pain or fever. They also had to have positive screening results for bacteriuria based on a test of a fresh, midstream urine specimen using a leukocyte esterase strip. During the study, patients were not catheterized nor were they given systemic antimicrobials or anticoagulants. Informed consent was obtained from the patients and the clinical research was conducted following the guidelines for human experimentation of the Toronto General Hospital.

Study Design

The sample size was calculated, not to determine significant efficacy, but rather as a preliminary examination of safety and of potential for use in postantimicrobial suppository therapy.

Each study patient was given a three day supply of either norfloxacin (400 mg twice daily) or TMP/SMX (160 mg/800 mg). The allocation was blinded and random. Urine culture confirmed the presence or absence of bacteria ($\geq 10^5$ organisms per ml of urine) and if no organisms were detected, the therapy was discontinued on day 2. On day 3, each patient randomly received one capsule of freeze-dried lactobacillus or (as placebo) sterilized skim-milk powder to be used intravaginally. The suppositories were inserted twice weekly for two weeks, and then at the end of each of the next two months. Urine cultures were taken during follow-up visits at 48 hours, two weeks, five weeks, three months, and six months. At the same time, vaginal swabs were obtained and cultured semiquantitatively in MRS (deMan, Rogosa, Sharpe) agar to determine if lactobacilli were present and which types of flora were dominant.

Vaginal Suppositories

Lactobacillus casei var rhamnosus GR-1 and Lactobacillus fermentum B-54 were cultured for 24 hours at 37° C. with 10% carbon dioxide in MRS broth, washed in phosphate-buffered saline, and resuspended in 10% specially prepared skim-milk powder. To each size AA gelatin capsule was added 0.5 gm of lactobacilli, representing more than $1.6 \times 10^9$ organisms per vial. (These organisms have a long shelf life; their viability has been found to drop less than 10% within 12 months). The skim-milk powder was suspended in saline, sterilized, and placed in 0.5 g capsules identical to those containing the lactobacilli. Both types of capsules were then packaged in sterile plastic containers, which were randomly dispensed by the hospital pharmacy.

Outcomes Monitored

Two outcomes were monitored; (1) whether antimicrobial therapy eradicated the bacterial UTI and eliminated symptoms within three days, and (2) to what extent infections recurred. Asymptomatic and symtomatic bacteriuria were monitored. Adverse side effects were determined by questioning the patients about signs of rash, vomiting, diarrhea, nausea, irritation, or discharge. Cultures were taken to identify vaginal yeast and other potential pathogens.

Results

The most commonly isolated organisms were Escherichia coli (65%), followed by coagulase-negative staphylococci (15%), coliforms (13%), Klebsiella sp (5%), and Proteus sp (2%). All the organisms cultured were susceptible in vitro to norfloxacin and TMP/SMX. The three day norfloxacin therapy was marginally more effective than TMP/SMX (100% vs 95%) in eradicating UTI from the bladder; however, the difference was not statistically significant. Only one patient was removed from the study because of no growth of bacteria from the urine culture. No side effects were reported by or recorded for any other patients, nor did any patients show evidence of superinfection.

Six patients decided not to take suppositories because their infections had been cleared and they felt well. Two patients failed to return for their five-week appointment due to university exams and travel problems, and one patient dropped out of the study due to an unrelated pneumoniae. One woman moved out of the province and could not make the six month appointment. Overall, 31 of the original 41 patients complied well with the study regimen.

TABLE 1

Rates of eradication and recurrence of urinary tract infection (UTI) by type of therapy.

| Therapy | No. of Patients* | UTI Eradication | UTI Recurrences† |
|---|---|---|---|
| Norfloxacin | 20 | 20 (100%) | 4/14 (29%) |
| Plus lactobacilli (10) | 6 | | 2 |
| Plus placebo (10) | 8 | | 2 |
| Trimethoprim/ sulfamethoxazole | 20 | 19 (95%) | 7/17 (41%) |
| Plus lactobacilli (9) | 8 | | 1 |
| Plus placebo (11) | 9 | | 6 |

*All 40 patients were evaluated for eradication of UTI but nine did not return for long-term follow-up and so could not be included in recurrent UTI analysis.
†Net recurrence rates: with lactobacillus, 21%; with placebo, 47% (P = 0.27).

As shown in Table 1 above, the symptomatic UTI recurrence rate for norfloxacin-treated patients was 29% and for TMP/SMX treated patients was 41% (P=0.77, chi-square). In addition, one asymptomatic infection was detected. Only one patient had more than one infection (two detected) during the study. Recurrences of UTI were treated with a three-day course of norfloxacin. Recurrences for lactobacillus treated patients occurred at two weeks (one patient) and at three months (two patients), giving an overall recurrence rate of 21%. In comparison, patients given skim milk suppositories experienced a recurrence rate of 47% with recurrences at two weeks (three patients), five weeks (one), two months (two), and six months (two) (P=0.27, chi-square). The causative organisms in the recurrences were $E$ $coli$ (nine), coagulase-negative staphylococci (one), and enterococci (one). Lactobacilli were absent from the vaginas of 50% of the patients upon entry into the study. Treatment with lactobacilli resulted in a threefold increase in lactobacillus counts. Some patients who received specially prepared skim milk suppositories had an increase in their lactobacillus counts following therapy (eg. $4.4 \times 10^5$/ml lactobacilli in a vaginal swab specimen upon entry, $1.2 \times 10^6$/ml after two weeks, and $9.6 \times 10^6$/ml after two weeks, and $9.6 \times 10^6$ ml after five weeks), showing the ability of this agent to stimulate the patients' own lactobacilli.

The present study supports the prior art finding that norfloxacin and TMP/SMX are effective in eradicating acute, uncomplicated cystitis. In this study, the organisms causing recurrences were typical uropathogens, suggesting that suppositories did not induce infection by less common isolates. Patient compliance with the study regimen was fairly good, considering that the patient population comprised university students whose follow-ups were often dictated by exam schedules and departure from campus to return to homes outside Toronto. Indigenous lactobacilli were present in the vaginas of patients who received TMP/SMX therapy followed by specially prepared skim milk suppositories.

The use of lactobacillus suppositories was well received and although only a small dosage was given, patients experienced a low rate of recurrence of UTI, without side effects or candidal superinfection. The current alternative for patients with recurrent UTI is daily doses of antimicrobial agents, sometimes for as long as five years. The use of daily doses of antimicrobial agents, especially TMP/SMX, to kill or inhibit the growth of uropathogens is effective and is used by most urologists; however, with this treatment some breakthrough infections can occur, drug resistant pathogens can emerge, and lengthy patient compliance is required.

The present study was not designed to compare lactobacillus suppositories with prophylactic TMP/SMX. The sample size was not chosen for efficacy. However, the study does not show the safety of the approach, an acceptable degree of effectiveness with limited therapy, and a particular potential for combined use with TMP/SMX. This regimen would be useful for many women, as it is known that certain antimicrobial therapy can disrupt the urogenital flora for several weeks and can even induce recurrences of UTI.

It is anticipated that in some patients, twice weekly lactobacillus or skim milk or LGF therapy may be needed to achieve a protective flora.

Occasionally, the virulence of uropathogens and the extent of their urogenital colonization will require extended antimicrobial therapy to eradicate the infecting bacteria and provide lactobacillus with an opportunity to potentially protect the patient.

Thus, both methods offered a degree of protection for the patient, without any side effects, especially the lactobacillus.

EXAMPLE 2

A randomized, controlled clinical trial was carried out to compare the use of lactobacillus vaginal supplementation with the use of a LGF to reduce the incidence of uncomplicated, lower urinary tract infections (UTI) in adult, premenopausal women.

Materials and Methods

Patients

Fifty five healthy women, aged 22 to 49 years (mean 34±6), were accrued, having signed a voluntary consent form approved by the Health Review Board of the Toronto General Hospital.

Entry Criteria and Pre-Trial Work-Up

The entry criteria were: (i) a history of at least 4 UTI in the past 12 months, with each one having symptoms and requiring antibiotic therapy, and with at least two being documented by cultures ($\geq 10^5$ organisms/ml mid stream urine), or alternatively, be receiving long term ($\geq 3$ months) low dose antibiotic therapy to prevent recurrences of UTI, and have had one positive culture prior to starting the study; (ii) a full urological work up to ensure there was no urinary tract abnormalities. This included urine culture and sensitivity, KUB X-ray, ultrasound of abdomen or intravenous pyelogram, cystoscopy and uroflow plus ultrasound (within 12 months of entry). The urogenital flora was also cultured for baseline lactobacillus counts. In addition, the presence of a sexually transmitted disease (bacterial, viral, chlamydia) was ruled out by culture. Patients with sterile urine were entered into the study.

Patients were excluded if they had abnormal renal function (serum creatinine $\geq 110$ umol/l, upper limit 90 umol/l) and/or pyelonephritis, diabetes mellitus, abnormal serum glucose, a neurogenic bladder, if their antibiotic therapy could not be discontinued, or if they were on prednisone or immunosuppressive drugs.

Sample Size and Justification

Based upon the analysis of past data on symptomatic, culture-confirmed UTI in 26 women meeting study eligibility criteria, it was decided that a clinically significant reduction of 50% would require a sample size of 28 patients in each arm of the study. This included an allowance for a nonparametric analysis (Wilcoxon Sum Rank Test) requiring a further 16% increase in sample size, and allowance for up to 20% drop-out, loss to follow-up etc. Randomization was stratified by 8 or more UTI per year and those with 4 to 8 per year, and also by long term antibiotic use. The purpose was to try to get balanced treatment allocation among variables that may correlate with outcome. Whilst the numbers were small for subgroup analysis, the information was deemed useful to obtain.

Preparation of Lactobacillus and LGF Suppositories

Two known in the art Lactobacillus strains *L. casei* var *rhamnosus* GR-1 and *L. fermentum* B-54 were selected wherein the relatively hydrophillic GR-1 and hydrophobic B-54 had been shown to be well adherent to uroepithelial cells, to block to some degree adhesion by uropathogens, to produce inhibitory substances against *E.coli* and *Enterococcus faecalis*, to resist some antimicrobial agents and NONOXYNOL-9®, and to form coaggregates similar to those found in the vagina of healthy women.

The organisms were inoculated from frozen ($-70°$ C.) culture vials onto Lactobacillus MRS agar, an enriched medium. Following 48 hours culture at $37°$ C. in 5% $CO_2$, the organisms were checked for purity and subcultured into 3 ml MRS broth then 25 ml broth for another 2×24 hours. Finally, the cultures were grown in batch MRS broth to obtain sufficient yields for the study, then the organisms were washed in sterile saline, suspended in sterilized skim milk powder and freeze dried. The lyophilized bacteria were checked for purity and potency monthly for the duration of the study. The purity was maintained and the potency was found to over $1×10^9$ viable organisms per vial. The organisms were dispensed into 0.5 g aliquots in size 00 gelatin capsules. The capsules were transferred to the Pharmacy Department at the Toronto General Hospital, where they were stored at $4°$ C. and distributed to individual patients in a randomized manner to which the principal investigators were blinded.

The LGF was suspended in distilled water, autoclaved, then freeze dried and dispended as 0.5 g aliquots into size 00 gelatin capsules.

The research nurse instructed the patient on how to insert the suppositories into the vagina. The procedure was carried out prior to going to bed at night, and at weekly intervals for 12 months. During menstruation, the patient did not insert a suppository but recommenced the application immediately following menses. The patient was instructed not to have intercourse on the night of suppository insertion.

Follow-up, Outcome Measures and Measurement of Compliance

Patients were seen in follow-up visits within the first two weeks of commencing therapy, and at the end of each month. The visits were arranged, where possible, seven days after insertion of a suppository. At each visit, the following procedures were performed: (i) a mid-stream urine sample was provided for culture, (ii) a vaginal swab and pH measurement were taken by the nurse and lactobacillus numbers measured by semi-quantitative culture and adherence per 50 gram stained epithelial cells, (iii) the suppository vial was returned to assess compliance, (iv) the patient's diary was inspected and the patient questioned about compliance, side effects, symptoms, antibiotic therapy or other improved or adverse effects to her health, and (v) another suppository vial was dispensed by the pharmacy.

If the patient developed symptoms or UTI (urgency, frequency, dysuria, pyuria, suprapubic discomfort), she provided a mid-stream urine sample, preferably first morning, in a sterile container. She placed a MULTISTIX® strip (Ames) and dip-slide (McConkey's and blood agar) into the urine, as previously instructed, and read a positive result of the former by colour changes representing leukocytes (purple) and nitrites (pink) indicative of uropathogenic infection. She also took a vaginal specimen and sent the samples for immediate culture. Infection was confirmed with the finding of $\geq 10^5$ single species of gram negative bacteria or $\geq 10^4$ single species of gram positive cocci per ml urine. The patient instituted three days of antibiotic therapy (norfloxacin 400 mg×2 or an alternative). If the culture turned out to be negative or with insignificant counts, the nurse recorded the results as institution of antibiotic therapy without infection. The infected patient was instructed to commence suppository insertion immediately after antibiotic use, and to send a urine sample for culture within one week to ensure eradication of infection. If the patient continued to have symptoms, along with bacteriuria upon one week follow-up, she ceased suppository use and was given 7–10 days antibiotics, based upon sensitivity to a drug. Lactobacillus or LGF therapy was commenced immediately upon completing use of the drugs.

If an episode of asymptomatic bacteriuria ($\geq 10^5$ uropathogenic bacteria per ml mid-stream urine) was detected upon routine monthly check-up, the patient was asked to self test her urine twice daily with a MULTISTIX® dip-strip. If there was a persistent positive result over one week confirmed by one additional culture, antibiotic administration was initiated and she followed the protocol for symptomatic infection.

Results

The drop out rate for the study was as predicted (22%), and the total patient accrual was also as expected (24 in LGF and 25 in lactobacillus group). Only six of the fifty five patients were excluded within the first two weeks of study due to never having complied (4) and being found to be pregnant within the first two weeks of study. (2) Eleven patients did not complete the full 12 month study due to recurrences of UTI (4), moving home (4), pregnancy later in the study (2) and receiving other therapy (1).

The results are shown in Table 2 below:

TABLE 2 the results for the clinical study of lactobacillus and LGF treated patients

| Lactobacillus Treated | | | | | LGF Treated | | | | |
|---|---|---|---|---|---|---|---|---|---|
| Pat# | Prev UTI | LTT | Study Time | Symp UTI | Pat# | Prev UTI | LTT | Study Time | Symp UTI |
| 101 | 5 | N | 51 | 1 | 103 | 4 | Y | 52 | 1 |
| 102 | 4 | Y | 52 | 0 | 104 | 7 | Y | 52 | 0 |
| 107 | 4 | N | 52 | 1 | 105 | 4 | Y | 52 | 1 |
| 108 | 4 | N | 55 | 2 | 106 | 4 | N | 52 | 2 |
| 112 | 7 | N | 52 | 0 | 109 | 4 | N | 52 | 0 |

TABLE 2-continued the results for the clinical study of
lactobacillus and LGF treated patients

| | Lactobacillus Treated | | | | LGF Treated | | | |
|---|---|---|---|---|---|---|---|---|
| Pat# | Prev UTI | LTT | Study Time | Symp UTI | Pat# | Prev UTI | LTT | Study Time | Symp UTI |
| 113 | 4 | N | 51 | 1 | 110 | 4 | Y | 54 | 0 |
| 118 | 4 | N | 53 | 0 | 114 | 5 | N | 52 | 0 |
| 122 | 6 | Y | 52 | 4 | 117 | 5 | Y | 54 | 1 |
| 124 | 5 | Y | 52 | 0 | 119 | 4 | N | 52 | 4 |
| 125 | 4 | N | 52 | 0 | 121 | 4 | Y | 52 | 0 |
| 129 | 4 | N | 53 | 4 | 123 | 4 | N | 52 | 1 |
| 205 | 12 | Y | 54 | 3 | 127 | 4 | Y | 53 | 0 |
| 206 | 8 | N | 52 | 5 | 128 | 6 | Y | 54 | 1 |
| 210 | 6 | Y | 52 | 0 | 130 | 6 | Y | 53 | 1 |
| 219 | 7 | Y | 52 | 4 | 141 | 4 | Y | 52 | 1 |
| 349 | 4 | N | 52 | 0 | 202 | 8 | Y | 52 | 0 |
| 351 | 8 | Y | 52 | 1 | 207 | 7 | Y | 52 | 2 |
| | | | | | 208 | 12 | Y | 53 | 0 |
| | | | | | 215 | 8 | N | 56 | 1 |
| | | | | | 217 | 12 | N | 53 | 2 |
| | | | | | 301 | 4 | N | 54 | 2 |
| Did not complete study: | | | | | | | | | |
| 111 | 5 | N | 39 | 1 | 211 | 4 | Y | 16 | 1 |
| 116 | 4 | N | 20 | 1 | 216 | 12 | N | 15 | 2 |
| 126 | 4 | Y | 19 | 0 | 396 | 8 | Y | 12 | 0 |
| 204 | 10 | N | 32 | 3 | | | | | |
| 212 | 6 | Y | 17 | 4 | | | | | |
| 214 | 7 | Y | 35 | 2 | | | | | |
| 218 | 12 | Y | 16 | 1 | | | | | |
| 382 | 6 | Y | 16 | 3 | | | | | |

Pat# = patient identification number;
Prev UTI = number of UTI in previous 12 months;
LTT = patient on long term therapy (Y) or not on long term therapy (N) upon entry to study;
Study Time = in weeks;
Symp UTI = number of symptomatic urinary tract infections during the study.

The primary objective of the study was to examine how many UTI recurrences occurred with the two therapies. The results showed that very few (26) recurrences of UTI occurred over one year in a group of 17 lactobacillus treated patients who completed the trial, and 20 UTI's occurred in the LGF group. There was no statistical difference between the incidence of acute, symptomatic UTI per year in the lactobacillus treated group of 25 patients compared to the 24 who were treated with LGF suppositories (p=0.686). There was also no statistical difference with respect to the mean number of asymptomatic infections between the two groups (1.0 UTI per year for lactobacillus patients, 0.6 for LGF: p=0.357). There was a substantial decrease in the symptomatic UTI rate compared to the previous 12 months, for patients given lactobacilli (73.1% reduction) and those given LGF (81.1%). This translated into an average of 1.9 and 1.0 UTIs per year per patient in the lactobacillus and LGF treated groups respectively compared to 5.6 and 6.0 respectively for the previous year. In the combined group, most (67%) patients had 0–1 infections per year, while a subgroup of 6 women (12%) acquired 4 or more of the infections recorded.

Of the patients given lactobacillus, 12 had been on long term antibiotic therapy and they subsequently acquired 22 UTI on study compared to 19 UTI in the other 13 patients who had not been on long term antibiotic therapy (p=0.966). In the LGF treated group, 15 patients had previously been on antibiotic prophylaxis and they acquired 9 UTI (versus 14 UTI for the other 9 patients previously not on antibiotic prophylaxis).

Dipsticks were used to detect infections at home and in the clinic. Of a total of 524 tests, the dipsticks were found to give a true positive result confirmed by culture in 100/111 (90%) of cases, and a true negative result confirmed by culture in 225/413 (54%) of cases. This translated into a sensitivity of 35% (100/288) and specificity of 95% (225/236).

The recurrences of UTI were caused by standard uropathogens: E.coli (57%), streptococci (including E. faecalis) (16%), Klebsiella 10%, staphylococci (10%), coliforms (3%), Enterobacter (2%) and Proteus (2%).

The vaginal pH was found to range from 3.5 to 7.5 over the study, with mean monthly values of 4.6 to 5.0 for the lactobacillus treated patients and 4.6 to 5.0 for the LGF treated group (no statistical difference between the groups).

The Lactobacillus semi-quantitative viable counts from vaginal swabs were monitored prior to and during study. FIG. 1 shows the mean values for lactobacillus colonization and demonstrates that supplementation with L. casei GR-1 and L. fermentum B-54 and the use of LGF led to an increased viable count of lactobacilli from the baseline level every month throughout the study (except for month 4, $p \leq 0.5$). Although not statistically significant, there was a trend towards higher numbers of lactobacilli in the patients treated with GR-1 and B-54 than in the LGF treated group, especially after 7 months. The lactobacillus viable count for the patients given GR-1/B-54 therapy showed a trend (p=0.061) towards being greater during the second six months of the study, compared to the first six months. In addition, the symptomatic infection rate was lower during the last six month period when lactobacillus numbers were elevated (P=0.232). Colony morphology and gram stain analysis by the technician (using a blinded numbering system) showed that GR-1 and B-54 could be correctly differentiated from other lactobacilli in 76% of the specimens from patients given suppositories containing these organisms. It was evident that throughout the course of the study, GR-1 and B-54 were indeed present and viable every week after insertion.

The analysis of lactobacillus adhesion counts per vaginal epithelial cell showed no difference between the two groups for all samples tested (14 per cell for the lactobacillus treated versus 13 per cell for LGF treated). However, for the lactobacillus treated group, there were twice as many adherent lactobacilli present in patients with 0–1 UTIs per year compared to those with $\geq 2$ UTIs per year (mean 17 adherent per cell versus 9). A comparison of the adherence and viable count data showed that values between 0 to 9 bacteria per cell corresponded to viable counts with a mean $2.5 \times 10^6$, while values $\geq 17$ per cell corresponded to viable counts of $4.8 \times 10^6$, indicating a degree of correlation.

The primary analysis showed there to be no difference between the infection rates between the two treatment groups. Rather than suggest that the lactobacillus group showed no effect on the infection rate, there are many findings which indicate that the two modes of therapy did protect the patients. The entry criteria did not require the close patient scrutiny and UTI confirmation that occurred during the study, and therefore the infection rate for the past 12 months is just as likely to be higher as it is lower (for example, asymptomatic or symptomatic UTI may have occurred without being recorded). The infection rate during study was extremely low (1.9 and 1.0 per patient per year respectively for the lactobacillus and LGF groups) for such a high risk group of patients. This rate includes a subgroup of 6 patients who experienced 4 or more UTIs per year.

Twenty seven of the patients had been on long term antibiotic therapy. A prior art study was carried out with similar inclusion criteria to the present one, to investigate whether three antimicrobial regimens reduced the recurrence rate for UTI in 67 women. (Brumfitt W, Hamilton-Miller J M T, Gargon R A, Cooper J, Smith G W, 1983. Long-term prophylaxis of urinary infections in women: comparative trial of trimethoprim, methenamine hippurate and topical povidone-iodine. *J. Urol* 130: 1110–1114.) Using the same method as here to determine the decrease in the infection rate from the previous year, the study found there to be 2.3 infections per year using nightly trimethoprim (100 mg), 2.4 per year using a povidone-iodine perineal wash and 2.0 per year using 1,000 mg methanamine-hippurate every 12 hours. Twenty three per cent of patients dropped out prematurely from the antimicrobial study and side effects of nausea, vomiting, gastrointestinal reactions and vulval rash were reported. Although only one mild occurrence of a side effect was reported using trimethoprim, there was an 82% resistance rate in organisms taken from patients treated with this antibiotic. Clearly, the present trial stands up well with that antimicrobial study, with no side effects, no drug resistance and lower rates of UTI recurrence.

It did appear that the instilled lactobacilli survived and grew in the urogenital tracts of the patients, based upon the morphological identification of strains GR-1 and B-54 from vaginal cultures and cells, and from the increased lactobacillus colony counts following suppository insertion. This is an important ecological finding, as some scientists have questioned whether or not implanted organisms could survive in the host. From FIG. 1, it would appear that the colonization level increased during the second six month period of the study, particularly in the lactobacilli treated patients. This coincided with a reduced infection rate. Whether this finding means that the inserted lactobacilli took several months to become fully established remains to be verified.

One of the criteria for selecting strains *L. casei* var *rhamnosus* GR-1 and *L. fermentum* B-54 was their known adhesiveness to uroepithelial cells in vitro (64 and 39 bacteria per cell, respectively). Clearly, the levels of adhesion found in vivo were much lower. This could have been due to their freeze dried status when implanted, to the difference in nutrients available compared to the in vitro assays, to a difference in receptor sites between the sloughed uroepithelial cells and vaginal cells, or reasons unknown. Similar discrepancies have been found for uropathogenic *E. coli* adherence in vivo and in vitro. A previous clinical study (Bruce et al., "Preliminary study on the prevention of recurrent urinary tract infection in adult women using intravaginal lactobacilli", Int Urogynecol J (1992)3:22–25) using intravaginal lactobacilli showed that an adhesion count greater than 4 bacteria per cell correlated with viable counts greater than 100,000 lactobacilli. In the present study, there was clearly substantial in vivo colonization: if each cell has 17 adherent lactobacilli, then only $2.82 \times 10^5$ cells would need to be coated to correspond to $4.8 \times 10^6$ viable organisms. This is not an unrealistic expectation considering that this number of vaginal cells, side by side, would only cover a 3 $cm^2$ surface area. Alternatively, the organisms could be colonizing the vaginal mucus and not be adherent to cells.

An interesting secondary finding was the very low (35%) sensitivity and very high (95%) specificity of the leukocyte nitrite dipsticks for detection of bacteriuria. This indicates some degree of use in the specificity of this quick method to determine whether or not a patient is suffering from UTI, but it also showed there are serious limitations to the sensitivity of the results.

There was no statistically significant difference in the infection rate for the two groups over the study. Based upon the UTI rate for the previous 12 months, there was a net 73.1% reduction in the symptomatic infection rate for patients given lactobacilli, and 81.1% reduction for those patients whose indigenous flora was stimulated with LGF. Most of the recurrences occurred in a small group of patients and all were caused by common uropathogens, with *E. coli* being responsible for 57%. No significant side effects arose during the study. The lactobacillus viable counts in the vagina were higher than the pretrial baseline values for both groups, but especially after 7 months of lactobacillus therapy. There were twice as many adherent lactobacilli per vaginal epithelial cell for patients with 0–1 UTIs per year compared to those with 2 or more per year. In summary, this example shows that recurrent UTI can be reduced in high risk patients using the two new prophylactic measures tested.

EXAMPLE 3

In order to confirm that LGF had a specific role in stimulating the indigenous lactobacillus flora of patients, a study was carried out on 13 healthy adult female volunteers. Their indigenous lactobacillus count was measured by swab and culture and taken as a baseline figure. Then, a single LGF vaginal suppository was administered and the patients returned one week later for vaginal swab and culture. The results shown in the Table 3 below demonstrate very clearly the significant impact (81.4% increase) of the therapy on the protective lactobacillus flora.

TABLE 3

The results of lactobacillus vaginal counts after treating 13 women with a single specially prepared suppositories containing lactobacillus nutrients. In all 13 specimens, the lactobacillus total vaginal count increased by a percentage means of 81.4 ± 19.7 over one week.

| Patient Number | Lactobacillus Viable Prior to Treatment | Counts per ml After Treatment | Percentage Difference |
|---|---|---|---|
| 1 | 5,000 | 361,000 | +99% |
| 2 | 7,000 | 132,000 | +95% |
| 3 | 6,000 | 165,000 | +96% |
| 4 | 6,800 | 34,000 | +80% |
| 5 | 1,000 | 28,000 | +96% |
| 6 | 1,800,000 | 2,880,000 | +38% |
| 7 | 25,300 | 50,000 | +49% |
| 8 | 700,000 | 5,000,000 | +86% |
| 9 | 6,500 | 256,000 | +97% |
| 10 | 70,000 | 370,000 | +81% |
| 11 | 180,000 | 6,200,000 | +97% |
| 12 | 4,000 | 9,000 | +56% |
| 13 | 2,000 | 17,000 | +88% |

EXAMPLE 4

The application further supports an earlier finding in 10 women who were given the lactobacillus suppositories once or twice weekly for over one year (Bruce et al., supra). In that group, there was a net resultant reduction in bladder infection rate of 77.3%. This is again a highly significant result and provides strong support for the claims, especially as the strains have been shown to possess specific hydrophobic and hydrophilic properties and produce cellular and extracellular adhesins. In this latter study, the adhesion of lactobacillus had to achieve $\geq 10^5$ organisms per ml when a mucosal tissue swab was taken and suspended for culture.

The use of different dosages was found to depend upon the patient's receptivity for lactobacilli, with more than one weekly treatment sometimes being required. Again, no serious side effects were found.

EXAMPLE 5

The characteristics of the lactobacillus are most important for their selection. The first is their ability to colonize surfaces. The organisms can achieve this through hydrophobic and hydrophilic mechanisms of binding to biomaterial (catheters, prosthetic devices) and cell (intestinal, vaginal, uroepithelial) surfaces. Hydrophobicity can be well measured using a technique called contact angle with water. The higher the angle, the more hydrophobic the organism. The testing of 23 strains, as shown in Table 4 below, has shown that the contact angle should be >19 degrees for lactobacillus to have adherence characteristic potential.

TABLE 4

| Adhesive Lactobacilli | | Water Contact Angle |
|---|---|---|
| L. acidophilus | 68 | 74 |
| | 75 | 66 |
| | RC-14 | 102 |
| | T-13 | 80 |
| L. casei | 55 | 36 |
| | 8 | 30 |
| | 43 | 46 |
| | 36 | 19 |
| | 62 | 19 |
| | 65 | 58 |
| | 70 | 43 |
| | ATCC 7469 | 34 |
| | RC-15 | 52 |
| | RC-17 | 54 |
| | GR-1 | 33 |
| | 81 | 86 |
| L. fermentum | A-60 | 29 |
| | B-54 | 105 |
| L. gasseri | 56 | 90 |
| | 60 | 67 |
| L. jensenii | RC-28 | 87 |
| L. plantarum | RC-6 | 25 |
| | RC-20 | 79 |

EXAMPLE 6

The adhesion of lactobacillus to cells is not a new finding, as we have shown in our 1987 J. Urology paper (Reid et al., "Examination of strains of lactobacilli for properties that may influence bacterial interference in the urinary tract", J. Urol., 138:330–335, 1987), nor is their adhesion to biomaterials, as we have shown in our 1988 Microbial Ecology paper (Reid et al., "Adhesion of lactobacilli to polymer surfaces in vivo and in vitro", Microb. Ecol. (1988) 16:241–251). However, adhesion per se is not sufficient, as in vitro experiments do not adequately reflect in vivo quantitative situations. This is shown from our clinical study of 10 patients where adhesion per cell varied from 0 to 45 per cell. Thus, the documentation of adhesion in vitro does not necessarily demonstrate that the bacteria will be adherent in vivo. This means that other adhesion characteristics are of importance and the models we test them on must be more realistic and utilize actual human cells in monolayers and commercially used catheters or devices that are in place within the urinary tract. To that end, lactobacilli have been found to adhere (>1000 per cm squared) to urinary catheters depending upon their own hydrophobic/hydrophilic properties. In addition, using human intestinal Caco-2 and HT-29 cell lines, lactobacilli (strains RC-17, RC-14, RC-20 and others) were found to adhere highly (often >60 bacteria per cell). Because uropathogenic organisms emerge from the intestine, lactobacillus should be used to compete with these within the intestine, thereby lowering the risk of the pathogens infecting the urogenital tract. It should be noted that this application can apply to males and females. This latest finding represents a different and not obvious use of lactobacillus implantation into the intestine. It also shows the colonization ability of strains to in vivo cells.

In addition, the mechanisms of adhesion for lactobacilli to the intestinal epithelial cells was via a non-proteinaceous cell wall adhesion, and especially a trypsin sensitive adhesion in the cell supernatant, i.e. produced by the cells. This is a new finding, and stresses that cell supernatants should be used in therapeutic regimens.

Adhesion of lactobacilli to biomaterial surfaces was found to be mediated by hydrophobic and hydrophillic mechanisms, again a novel discovery.

EXAMPLE 7

The ability of the lactobacillus to resist NONOXYNOL-9® is one characteristic that is of general importance. However this property does not improve adhesion, thus it is not a vital component of the successful selection of the organisms. The key to having lactobacilli resistant to NONOXYNOL-9® is that for patients who administer NONOXYNOL-9® (contained within a spermicide) used as an adjunct to a condom or other contraception, the installation of lactobacillus will be vital to balance the flora. Our previous studies (McGroarty et al., "Influence of the Spermicidal Compound Nonoxynol-9 on the growth and adhesion of urogenital bacteria in vitro", Current Microbiology, Vol. 21 (1990), pp. 219–223) have shown that NONOXYNOL-9® usually kills lactobacilli and allows urogenital bacterial and fungal pathogens to grow and potentially dominate the flora and infect the patient. The selection of lactobacilli that resist NONOXYNOL-9® has now been developed and tested in the three clinical studies described above. There are no adverse effects of using NONOXYNOL-9® resistant strains, but the patient using this spermicidal compound will likely have fewer urogenital infections. This acts as an example of the benefits of resisting the action of an antimicrobial agent.

EXAMPLE 8

Unlike other definitions of lactobacillus for human use, we have found the production of inhibitory substances, such as hydrogen peroxide, need not be essential for effectiveness. In a study of over 150 normal women and women with a history of recurrent urogenital (yeast and bacterial) infections, we found that hydrogen peroxide producing lactobacilli were isolated from either group, thus showing that this inhibitory substance does not play a major role in defending the host against infection. This study also isolated and speciated strains from women, and demonstrated the species of lactobacillus which form the flora of the urogenital tract.

EXAMPLE 9

Of over 150 strains in our collection, most show an ability to resist more than one antimicrobial agent. In the case of vancomycin resistance, this appears to correlate to some extent with hydrophilic surface properties and NONOXYNOL-9® resistance, as shown in Table 5 below. Thus, the surface components that confer adhesiveness also impart resistance to antimicrobial agents. This represents a novel finding.

agents. Table 6 below is an example of antimicrobial susceptibility patterns:

TABLE 6

Example of Antimicrobial Susceptibility Patterns

|  | AM | AN | C | CC | CF | E | NN | P | S | SXT | Te | Va | NO. OF STRAINS TESTED |
|---|---|---|---|---|---|---|---|---|---|---|---|---|---|
| L. Jensenii | S | S | S | S | S | S | S | S | S | R | S | S | 3 |
|  | S | R | S | S | S | S | R | S | R | R | S | S | 1 |
|  | S | S | S | R | S | S | S | S | S | S | R | S | 1 |
|  | S | S | S | S | S | S | S | S | R | S | S | S | 1 |
|  | S | R | S | S | S | S | R | S | S | R | S | S | 1 |
|  | S | R | S | S | S | S | R | S | R | R | S | R | 1 |
|  | S | R | S | S | S | S | R | S | S | R | S | R | 3 |
| L. Casei | S | R | S | R | S | S | R | S | S | R | S | R | 1 |
|  | S | R | S | S | S | S | R | S | S | R | S | R | 4 |
|  | S | R | S | S | S | S | R | S | S | R | S | R | 2 |
|  | R | R | S | S | S | S | R | S | R | R | S | R | 1 |
|  | R | R | S | R | S | S | R | R | R | R | S | R | 1 |
|  | S | R | S | R | R | S | S | R | R | R | S | R | 1 |
|  | S | R | S | S | S | S | R | S | R | R | S | S | 1 |
|  | S | R | S | R | S | S | R | S | R | R | S | S | 1 |
| L. Acidophilus | S | R | S | R | R | S | S | S | R | R | S | S | 2 |
|  | S | R | S | S | S | S | R | S | R | R | S | S | 3 |
|  | S | R | S | R | S | S | R | S | S | R | S | S | 1 |
|  | S | S | S | S | S | S | R | S | R | R | S | R | 1 |
|  | S | R | S | S | S | S | R | S | S | R | S | S | 1 |
|  | S | S | S | R | S | S | R | S | R | R | S | S | 1 |
|  | S | R | S | R | S | S | R | S | R | R | S | S | 1 |
| L. Fermentum | R | S | S | S | R | S | R | S | R | R | R | R | 1 |
| L. Plantarum | S | R | S | R | R | R | R | R | R | R | R | R | 1 |

R = Resistant, S = Susceptible
NOTE:
The antibiotics used were Amplicillin (AM), Amikacin (AN), Chloramphenicol (C), Clindamycin (CC), Cephalothin (CF), Erythromycin (E), Tobramycin (NN), Penicillin (P), Streptomycin (S), Sulfamethoxaxole/Trimethoprim (SXT), Tetracycline (T), Vancomycin (V).

TABLE 5

Hydrophobicity of lactobacilli and relationship with susceptibility to vancomycin and NONOXYNOL-9 ®

| Strain | Contact Angle (Degrees) | Vancomycin | NONOXYNOL-9 |
|---|---|---|---|
| L. casei 55 | 36 | S | S |
| L. gasseri 60 | 67 | S | S |
| L. acidophilus 68 | 74 | S | S |
| L. acidophilus 75 | 65 | S | S |
| L. plantarum RC-20 | 79 | S | S |
| L. casei RC-15 | 52 | S | S |
| L. jensenii RC-28 | 87 | S | S |
|  | Mean 66 ± 15 |  |  |
| L. casei 8 | 30 | R | R |
| L. casei 70 | 43 | R | R |
| L. casei GR-1 | 33 | R | R |
| L. casei 36 | 19 | R | R |
| L. casei 62 | 19 | R | R |
| L. casei 65 | 58 | R | R |
| L. plantarum RC-6 | 25 | R | R |
|  | Mean 32 ± 13 |  |  |

R = resistant, S = susceptible
Mean of 66 is significantly greater than 32 (Chi-squared test, $p < 0.001$).

In order for lactobacillus to survive and continue to protect the host, it is important that these organisms possess antimicrobial activity, particularly against co-trimoxazole, the most commonly used antimicrobial agent against bladder infection. Resistance to co-trimoxazole has been documented in our studies. The testing of 125 lactobacillus strains showed resistance to one or more antimicrobial

EXAMPLE 10

The use of lactobacillus within a skim milk powder or LGF base in a gelatin suppository results in a stable preparation >1000M viable organisms per 0.5 g over 12 months.

While the invention has been described in detail and with reference to specific embodiments thereof, it will be apparent one skilled in the art that various changes and modifications can be made therein without departing from the spirit and scope thereof.

The following microorganisms were deposited in the American Type Culture Collection, 12301 Parklawn Drive, Rockville, Md. 20852: Lactobacillus casei var rhamnosus, GR-1, ATCC 55826 on Oct. 3, 1996; Lactobacillus casei var rhamnosus, RC-17, ATCC 55825 on Oct. 3, 1996; Lactobacillus casei, RC-36, ATCC 55841 on Oct. 25, 1996; Lactobacillus plantarum, RC-20, ATCC 55883 on Nov. 26, 1996; Lactobacillus fermentum, B-54, ATCC 55884 on Nov. 26, 1996; Lactobacillus acidophilus, RC-14, ATCC 55845 on Oct. 25, 1996; Lactobacillus gasseri 60 on Oct. 25, 1996, ATCC 55844; and Lactobacillus jensenii, RC-28, ATCC 55918 on Dec. 19, 1996.

We claim:

1. A method for the prevention of urogenital infection in a mammal caused by pathogenic organisms which comprises administering to the mammal as an active agent, a therapeutically effective amount of skim milk powder, or skim milk powder and one or more Lactobacillus strains wherein said skim milk powder has been buffered, sterilized, and lyophilized.

2. The method of claim 1 wherein said Lactobacillus strain is selected from the group consisting of L. casei, L.

acidophilus, L. plantarum, L. fermentum, L. jensenii, L. gasseri, L. cellobiosis, L. crispatus, and L. brevis.

3. The method of claim 2 wherein said Lactobacillus strain is selected from the group consisting of L. casei var. rhamnosus GR-1, L. fermentum B-54, L. casei RC-17, L. casei RC-36, L. acidophilus RC-14, L. plantarum RC-20, L. jensenii RC-28 and L. gasseri 60.

4. The method of claim 1 wherein said pathogenic organisms are bacteria or fungi.

5. The method of claim 1 wherein said administration is by vaginal suppository.

6. A method for the prevention of recurrent urogenital infections in a mammal caused by pathogenic organisms comprising the steps of: a) administering to the mammal a therapeutically effective amount of a urogenital antimicrobial agent to effectively eradicate said pathogenic organisms; and b) administering to the mammal a therapeutically effective amount of skim milk powder, or skim milk powder and one or more Lactobacillus strains wherein said skim milk powder has been buffered, sterilized, and lyophilized.

7. The method of claim 6 wherein said Lactobacillus strain is selected from the group consisting of L. casei, L. acidophilus, L. plantarum, L. fermentum, L. jensenii, L. gasseri, L. cellobiosis, L. crispatus, and L. brevis.

8. The method of claim 7 wherein said Lactobacillus strain is selected from the group consisting of L. casei var. rhamnosus GR-1, L. fermentum B-54, L. casei RC-17, L. casei RC-36, L. acidophilus RC-14, L. plantarum RC-20, L. jensenii RC-28 and L. gasseri 60.

9. The method of claim 6 wherein said pathogenic organisms are bacteria or fungi.

10. The method of claim 6 wherein said administration of said skim milk or said skim milk and said Lactobacillus strain is by vaginal suppository.

11. A method for the prevention of urogenital infections in a mammal caused by pathogenic organisms which comprises coating a portion of a urinary prosthetic device with skim milk powder, or skim milk powder and one or more Lactobacillus strains wherein said skim milk powder has been buffered, sterilized, and lyophilized, and then inserting the coated prosthetic device in the mammal in need thereof.

12. The method of claim 11 wherein said Lactobacillus strain is selected from the group consisting of L. casei, L. acidophilus, L. plantarum, L. fermentum, L. jensenii, L. gasseri, L. cellobiosis, L. crispatus, and L. brevis.

13. The method of claim 12 wherein said Lactobacillus strain is selected from the group consisting of L. casei var. rhamnosus GR-1, L. fermentum B-54, L. casei RC-17, L. casei RC-36, L. acidophilus RC-14, L. plantarum RC-20, L. jensenii RC-28 and L. gasseri 60.

14. The method of claim 11 wherein said pathogenic organisms are bacteria or fungi.

15. A method for the prevention of urogenital infection in a mammal caused by pathogenic organisms which comprises administering to the mammal a therapeutically effective amount of skim milk powder that has been buffered, sterilized, and lyophilized.

16. A method for the prevention of urogenital infections in a mammal caused by pathogenic organisms comprising the steps of: (a) administering to the mammal a therapeutically effective amount of a urogenital antimicrobial agent to effectively eradicate said pathogenic organisms; and (b) administering to the mammal a therapeutically effective amount of skim milk powder that has been buffered, sterilized, and lyophilized.

* * * * *